US007608458B2

(12) United States Patent
Soykan et al.

(10) Patent No.: US 7,608,458 B2
(45) Date of Patent: Oct. 27, 2009

(54) IDENTIFYING PATIENTS AT RISK FOR LIFE THREATENING ARRHYTHMIAS

(75) Inventors: Orhan Soykan, Shoreview, MN (US); Amy C. Dearking, Rochester, MN (US); Timothy H. Robinson, Savage, MN (US); Walter H. Olson, North Oaks, MN (US); Vinod Sharma, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 842 days.

(21) Appl. No.: 11/157,549

(22) Filed: Jun. 21, 2005

(65) Prior Publication Data
US 2005/0266576 A1 Dec. 1, 2005

Related U.S. Application Data

(63) Continuation-in-part of application No. 11/050,611, filed on Feb. 3, 2005.

(60) Provisional application No. 60/542,004, filed on Feb. 5, 2004.

(51) Int. Cl.
*G01N 33/00* (2006.01)
(52) U.S. Cl. .................. 436/86; 800/508; 800/515
(58) Field of Classification Search .............. 436/86; 600/508, 515
See application file for complete search history.

(56) References Cited

U.S. PATENT DOCUMENTS 5,018,067 A    5/1991  Mohlenbrock
5,437,285 A    8/1995  Verrier
6,099,469 A    8/2000  Armstrong
6,210,976 B1   4/2001  Sabbadini
6,274,332 B1   8/2001  Keating
6,306,087 B1  10/2001  Barnhill
6,368,823 B1   4/2002  Bril
6,432,644 B1   8/2002  Keating
6,458,542 B1  10/2002  George, Jr. et al.
6,500,630 B2 * 12/2002  Conover et al. ............ 435/7.94
6,571,129 B2   5/2003  Schaldach
6,597,952 B1   7/2003  Mika (Continued)

FOREIGN PATENT DOCUMENTS

EP    0721786 B1    7/1996

(Continued)

OTHER PUBLICATIONS

Ken Rubenstein, Ph.D., Post-Genomic Biomarkers: Revolutionizing Drug Development and Diagnostics, Report #9129, Sep. 2003, D&MD Publications.

(Continued)

*Primary Examiner*—Michael A Marcheschi
*Assistant Examiner*—Jonathan M Hurst
(74) *Attorney, Agent, or Firm*—Hahn & Voight PLLC; Roger C. Hahn

(57) ABSTRACT

The invention is a method for identifying proteins associated with sudden cardiac death (SCD) and for assessing a patient's risk of SCD by determining the amount of one or more SCD-associated proteins in the patient. Typically, the patient submits a sample, such as a blood sample, which is tested for one or more SCD-associated proteins. Based upon the results of the tests, the patient's risk of SCD may be assessed.

25 Claims, 7 Drawing Sheets

U.S. PATENT DOCUMENTS

| | | | |
|---|---|---|---|
| 6,647,341 | B1 | 11/2003 | Golub |
| 7,208,273 | B2 | 4/2007 | Keating |
| 2002/0049772 | A1 | 4/2002 | Rienhoff, Jr. |
| 2002/0059030 | A1 | 5/2002 | Otworth |
| 2002/0076809 | A1 | 6/2002 | Steinmeyer et al. |
| 2002/0077470 | A1 | 6/2002 | Walker |
| 2002/0086297 | A1 | 7/2002 | Siffert |
| 2002/0115073 | A1 | 8/2002 | Papadopoulos |
| 2002/0155539 | A1 | 10/2002 | Ruben et al. |
| 2002/0165161 | A1 * | 11/2002 | Allison ........................ 514/12 |
| 2002/0182599 | A1 | 12/2002 | Fishman |
| 2003/0004402 | A1 | 1/2003 | Hitt |
| 2003/0096782 | A1 | 5/2003 | Bristow |
| 2003/0108924 | A1 | 6/2003 | George, Jr. et al. |
| 2003/0162192 | A1 | 8/2003 | Sotos |
| 2003/0175795 | A1 | 9/2003 | Walker |
| 2003/0198970 | A1 | 10/2003 | Roberts |
| 2003/0228565 | A1 | 12/2003 | Oestreicher |
| 2003/0235838 | A1 | 12/2003 | Keating |

FOREIGN PATENT DOCUMENTS

| | | |
|---|---|---|
| EP | 0842475 B1 | 2/1997 |
| EP | 1100825 B1 | 2/2000 |
| EP | 1176197 A1 | 1/2002 |
| WO | 95/15116 | 6/1995 |
| WO | 96/28537 | 9/1996 |
| WO | 98/09226 | 3/1998 |
| WO | 99/27140 A1 | 6/1999 |
| WO | 99/51778 A1 | 10/1999 |
| WO | 99/67628 A1 | 12/1999 |
| WO | 01/81895 A2 | 11/2001 |
| WO | 01/92567 A2 | 12/2001 |
| WO | 02/052033 A1 | 7/2002 |
| WO | 02/086447 A2 | 10/2002 |
| WO | WO 03/002757 A1 | 1/2003 |
| WO | WO 03/006687 A1 | 1/2003 |
| WO | 03/040407 A2 | 5/2003 |
| WO | WO 2004/005931 | 1/2004 |

OTHER PUBLICATIONS

D. Kent Arrell, et al., Cardiovascular Proteomics, Evolution and Potential, Circ. Res. 2001; 88:pp. 763-773.

Urban A. Kiernan, Comparative Urine Protein Phenotyping Using Mass Spectrometric Immunoassay, Journal of Proteome Research.( 2003 ).

Eleftherios P. Diamandis, Proteomic Patterns in Biological Fluids: Do They Represent the Future of Cancer Diagnostics?, Clinical Chemistry 49:8, pp. 1272-1278. (2003).

Emanuel F. Petricoin, III, et al., Use of Proteomic Patterns in Serum to Identify Ovarian Cancer, The Lancet, vol. 359, Feb. 16, 2002, pp. 572-577.

Urban A. Kiernan, Comparative Urine Protein Phenotyping Using Mass Spectrometric Immunoassay, Journal of Proteome Research.

Eleftherios P. Diamandis, Proteomic Patterns in Biological Fluids: Do They Represent the Future of Cancer Diagnostics?, Clinical Chemistry 49:8, pp. 1272-1278.

Fananapazir, et al., Genotype-Phenotype Correlations in Hypertrophic Cardiomyopathy: Insights Provided by Comparisons of Kindreds with Distinct and Identical Beta-myosin Heavy Chain Gene Mutations, Circulation, 1994; 89 (1): 22-32.

Samani, et al., A Meta-analysis of the Association of the Deletion Allele of the Angiotensin-Converting Enzyme Gene with Myocardial Infarction, Circulation, 1996; 94: 708-12.

Aronsky, et al., An Integrated Decision Support System for Diagnosing and Managing Patients with Community-Acquired Pneumonia, Proc. AMIA Symp., 1999; 197-201.

Colombet, et al., Decision Aids for Triage of Patients with Chest Pain: A Systematic Review of Field Evaluation Studies, Proc. AMIA Symp., 1999; 231-35.

Jouven, et al., Predicting Sudden Death in the Population: The Paris Prospective Study I, Circulation, 1999; 99: 1978-83.

Dunn, Studying Heart Disease Using the Proteomic Approach, Drug Discovery Today, Feb. 1, 2000; 5(2): 76-84.

Jouven et al., Circulating Nonesterified Fatty Acid Level as a Predictive Risk Factor for Sudden Death in the Population, Circulation, 2001; 101: 756-61.

Iwasa, et al., Multiple Single-Nucleotide Polymorphisms (SNPS) in the Japanese Population in Six Candidate Genes for Long QT Syndrome, J. Hum. Genet., 2001; 46: 158-62.

Christodoulides, et al., A Microchip-Based Multianalyte Assay System for the Assessment of Cardiac Risk, Analytical Chemistry, 2002; 74(13): 3030-36.

Moss, et al., Increased Risk of Arrhythmic Events in Long-QT Syndrome with Mutations in the Pore Region of the Human Ether-a-go-go-Related Gene Potassium Channel, Circulation, 2002; 105: 794-99.

Iwasa, et al., Twenty Single-nucleotide Polymorphisms in Four Genes Encoding Cardiac Ion Channels, J. Hum. Genet., 2002; 47(4): 208-12.

Hirschhorn, et al., a Comprehensive Review of Genetic Association Studies, Genetics in Medicine, 2002; 4(2): 45-61.

Frank-Hansen, et al., Mutations in the Genes KCND2 and KCND3 Encoding the Ion-Channels Conducting the Cardiac Transient Outward Current (ITO) is not a Frequent Cause of Long QT Syndrome, Am. J. Hum. Genet., 2002; 71(4 Supp.): 521.

Issaq, et al., the SELDI-TOF MS Approach to Proteomics: Protein Profiling and Biomarker Identification, Biochemical and Biophysical Research Communications, Apr. 5, 2002; 292(3): 587-92.

Hegele, SNP Judgments and Freedom of Association, Arteriosclerosis, Thrombosis, and Vascular Biology, 2002; 22: 1058-61.

Splawski, et al., Variant of SCN5A Sodium Channel Implicated in Risk of Cardiac Arrhythmia, Science, Aug. 23, 2002, 297:1333-36.

Danne, et al., Prognostic Implications of Elevated Whole Blood Choline Levels in Acute Coronary Syndromes, The Am. J. Cardiology, May 1, 2003; 91(9): 1060-67.

Dhar et al., Prognostic significance of metastatic lymph node size in patients with gastric cancer, British J. of Surgery, 2003; 90: 1522-30.

Kuzuya et al., Report of the Committee on the classification and diagnostic criteria of diabetes mellitus, Diabetes Res. and Clin. Practice, 2002; 55: 65-85.

* cited by examiner

US 7,608,458 B2

IDENTIFYING PATIENTS AT RISK FOR LIFE THREATENING ARRHYTHMIAS

CROSS-REFERENCE TO RELATED APPLICATION(S)

This application is a continuation-in-part of Ser. No. 11/050,611, filed Feb. 3, 2005, which claims priority from U.S. Provisional Application No. 60/542,004, filed Feb. 5, 2004.

This application is related to the application entitled "Self-Improving Classification System" and "Self-Improving Identification Medthod," which were filed on the same day and also assigned to Medtronic, Inc.

BACKGROUND OF THE INVENTION

The present invention relates to a system and method for identifying candidates for receiving cardiac therapy based on biochemical markers associated with propensity for arrhythmias.

Many patients experiencing ventricular tachyarrhythmia may be at risk of loss of heart function. Sudden cardiac death, which results from a loss of heart function, is often preceded by episodes of ventricular tachyarrhythmia such as ventricular fibrillation (VF) or ventricular tachycardia (VT). Many patients are unaware that they are at risk of ventricular tachyarrhythmia. For some unfortunate patients, a sudden cardiac death incident may be the first sign that they were at risk. It is of course preferable for such patients to be aware of their risk in advance of such an event. In patients who are aware of their risk, an implantable medical device, such as a pacemaker with defibrillation and cardioversion capability, may drastically increase the survival rates of such patients.

BRIEF SUMMARY OF THE INVENTION

In general, the invention is directed to systems and techniques for assessing a risk of ventricular tachyarrhythmia in a patient. In some medical conditions, including but not limited to ventricular tachyarrhythmia, certain biochemical factors in the body of the patient reflect the health of a patient. A patient that experiences ventricular tachyarrhythmia, for example, may experience an increased or decreased concentration of identifiable proteins in his/her blood, even if the patient is symptom free. By measurement of the concentration of these biochemical markers or "biomarkers" in the patient, an assessment of a risk of ventricular tachyarrhythmia for the patient can be made, based upon the measurements.

DETAILED DESCRIPTION

Figure 1:
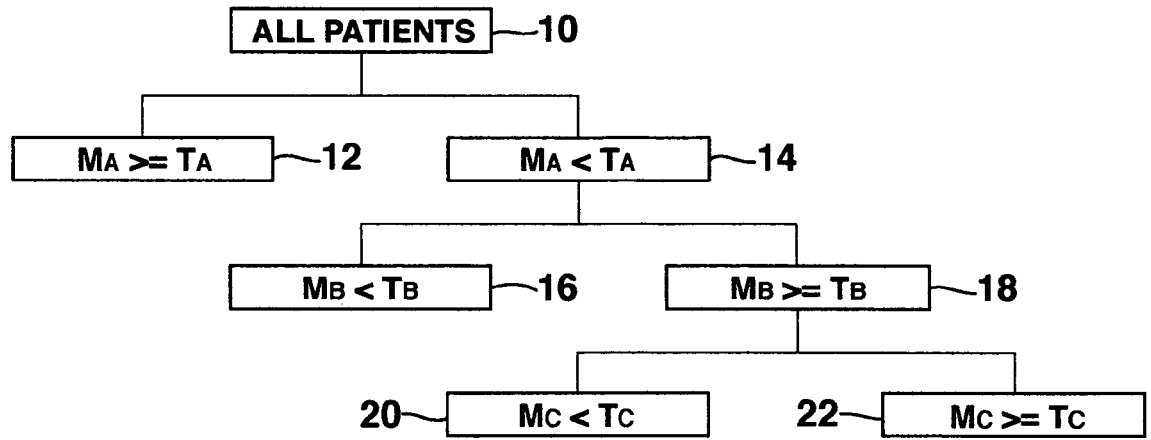
FIG. 1 is a conceptual logical diagram illustrating an embodiment of the invention.

FIG. 1 is a conceptual logical diagram illustrating an embodiment of the invention. Based upon measuring one or more biochemical markers in a group of patients 10, the invention provides for assessing a risk of ventricular tachyarrhythmia in each patient as a function of the measurement.

In the illustration shown in FIG. 1, a "tree analysis" sorts the patients into groups according to measurements of three biochemical markers. The biochemical markers are identified by the letters "A," "B," "C" and "D." Typical biochemical markers include proteins (that includes, for example, peptides, polypeptides, and polyamino acids of any length or conformation), lipids, genes and peptides or any combination thereof, but the illustration shown in FIG. 1 is not limited to any particular biochemical marker or set of biochemical markers. Specific examples of biochemical markers are discussed below.

For each patient, a measure of a first biochemical marker (denoted $M_A$) is determined. Determining the measure of biochemical marker "A" for a particular patient may include, for example, determining the concentration or mass of biochemical marker "A" in a standard sample of bodily fluid taken from that patient. For each patient, the measure of the first biochemical marker is compared to a threshold value (denoted $T_A$). Those patients for whom $M_A$ is greater than or equal to $T_A$ are deemed to be a group 12 that is not at significant risk of ventricular tachyarrhythmia, and no further testing need be done for the members of group 12. Those patients for whom $M_A$ is less than $T_A$ are deemed to be a group 14 that may be, or may not be, at risk of ventricular tachyarrhythmia. In FIG. 1, the members of group 14 undergo further testing to determine the individual members' risks of ventricular tachyarrhythmia.

For each patient in group 14, a measure of a second biochemical marker "B" (denoted $M_B$) is determined. For each patient in group 14, the measure of the second biochemical marker is compared to a second threshold value (denoted $T_B$) Those patients for whom $M_B$ is less than $T_B$ are deemed to be a group 16 that is not at significant risk of ventricular tachyarrhythmia, and no further testing need be done for the members of group 16. Those patients for whom $M_B$ is greater than or equal to $T_B$ are deemed to be a group 18 that may be, or may not be, at risk of ventricular tachyarrhythmia.

The members of group 18 undergo further testing with respect to a measure of a third biochemical marker "C" (denoted $M_C$). For each patient in group 18, the measure of the third biochemical marker is compared to a third threshold value (denoted $T_C$). On the basis of the comparison, the patients are divided into a group 20 that is not at significant risk of ventricular tachyarrhythmia, and a group 22 that is at significant risk of ventricular tachyarrhythmia.

In other words, FIG. 1 illustrates assessing a risk of ventricular tachyarrhythmia for a patient as a function of the measurement of three biochemical markers. Unless a patient meets the threshold criteria for all three biochemical markers, the patient will not be deemed to be at significant risk of ventricular tachyarrhythmia.

The thresholds $T_A$, $T_B$ and $T_C$ are determined empirically. Clinical studies and experience may be used to determine thresholds for each biochemical marker. The thresholds may differ from marker to marker. For some biochemical markers, a patient may be at higher risk when the measure of the biochemical marker is above the threshold, and for other biochemical markers, the patient may be at higher risk when the measure of the biochemical marker is below the threshold.

Figure 2:
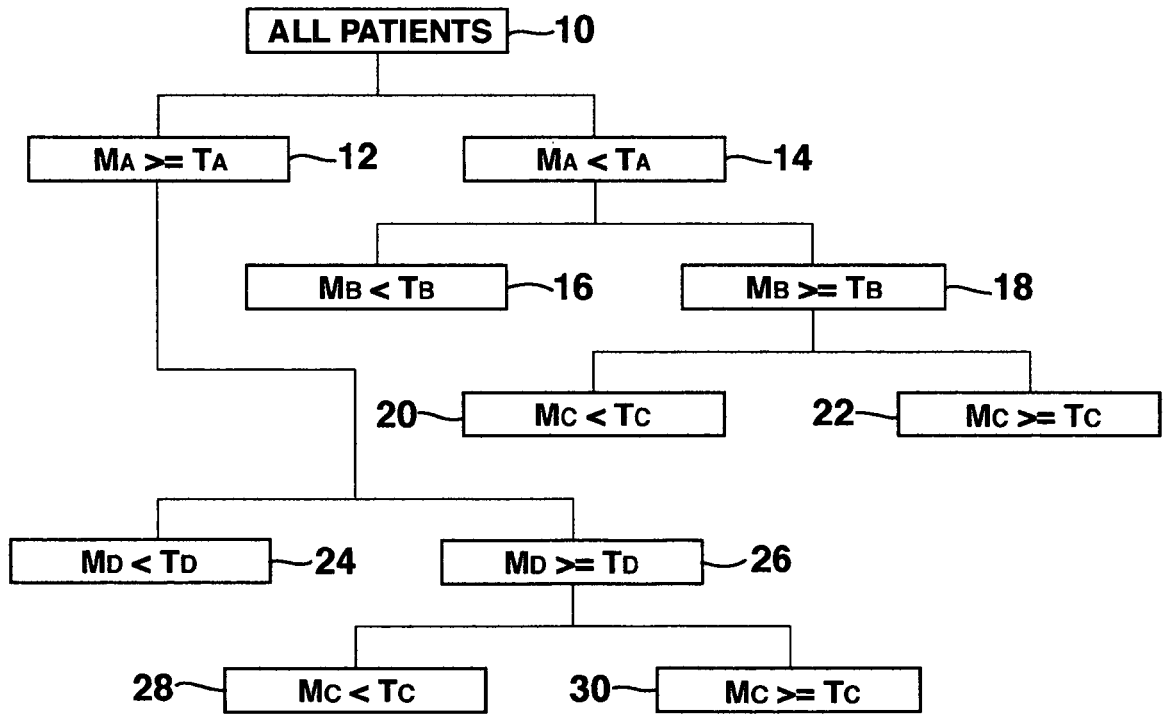
FIG. 2 is a conceptual logical diagram illustrating a variation of the embodiment of the invention shown in FIG. 1.

FIG. 2 is a conceptual logical diagram illustrating an embodiment of the invention that is a variation of the technique illustrated in FIG. 1. Unlike FIG. 1, patients sorted into group 12 are subjected to further testing. For each patient in group 12, a measure of a fourth biochemical marker "D" (denoted $M_D$) is determined, and the measure is compared to a fourth threshold value (denoted $T_D$). On the basis of this comparison, patients in group 12 are sorted into groups 24 and 26. Those patients in group 24 are deemed to be not at significant risk of ventricular tachyarrhythmia, and no further testing need be done for the members of group 24.

Those patients in group 26, however, are subjected to further testing. The members of group 26 undergo further testing with respect to the third biochemical marker "C," just like the members of group 18. On the basis of a comparison of the measure of the third biochemical marker to the third threshold, the patients in group 26 are divided into a group 28 that is not at significant risk of ventricular tachyarrhythmia, and a group 30 that is at significant risk of ventricular tachyarrhythmia.

In other words, FIG. 2 illustrates assessing a risk of ventricular tachyarrhythmia for a patient as a function of the measurement of four biochemical markers. A patient may be deemed to be at significant risk of ventricular tachyarrhythmia according to more than one testing path.

Figure 3:
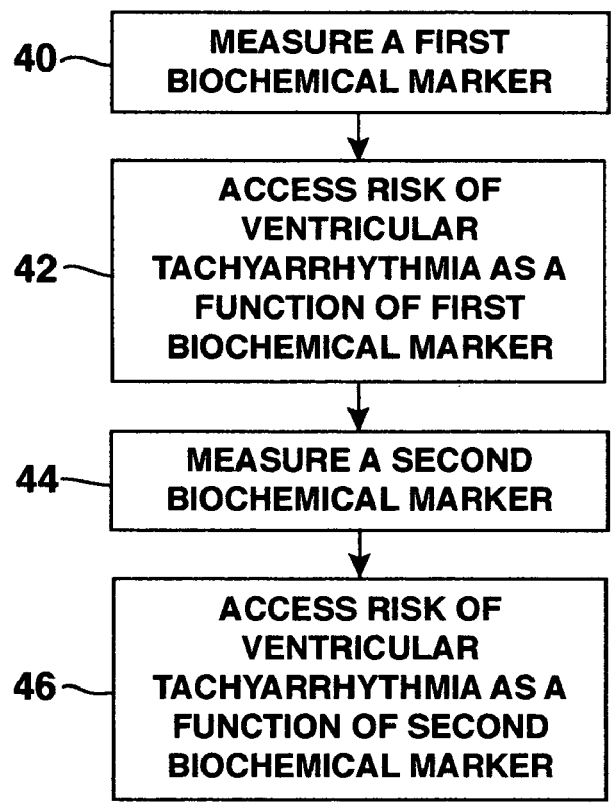
FIGS. 3 and 4 are flow diagrams illustrating techniques for assessment of risk of ventricular tachyarrhythmia.

FIG. 3 is a flow diagram illustrating logical sorting embodiments such as are depicted in FIGS. 1 and 2. An apparatus, such as apparatus illustrated in FIGS. 5 and 6, or a technician measures a first biological marker (40) and assesses a risk of ventricular tachyarrhythmia in the patient as a function of the measurement (42). The apparatus or technician measures a second biological marker (44) and assesses the risk of ventricular tachyarrhythmia in the patient as a function of that measurement (46).

Figure 4:
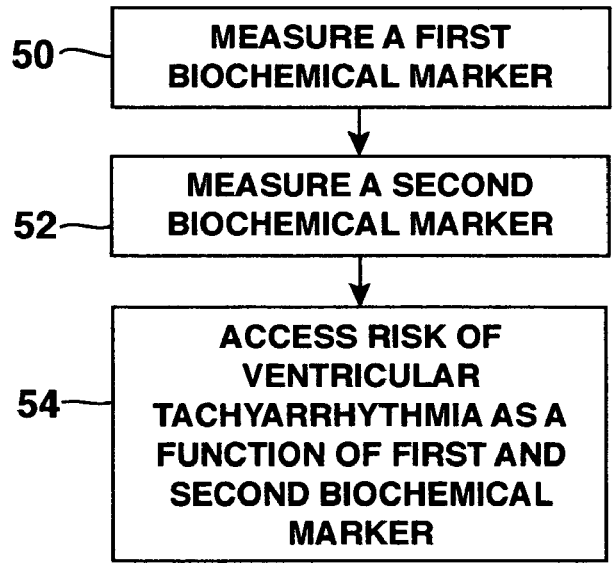

In the procedure outlined in FIG. 4, the apparatus or technician measures a first biological marker (50) and measures a second biological marker (52), and assesses the risk of ventricular tachyarrhythmia in the patient as a function of both measurements (54). The techniques shown in FIGS. 3 and 4 may achieve the same result, that is, a patient may be sorted according to risk of ventricular tachyarrhythmia using either technique. When a patient is deemed to be at risk, an appropriate therapy may be applied. Therapy for a patient may include, for example, implanting an electronic cardiac stimulation device in the patient that detects and terminates episodes of ventricular tachyarrhythmia or administering an antiarrhythmic drug that prevents induction of such episodes.

Figure 5:
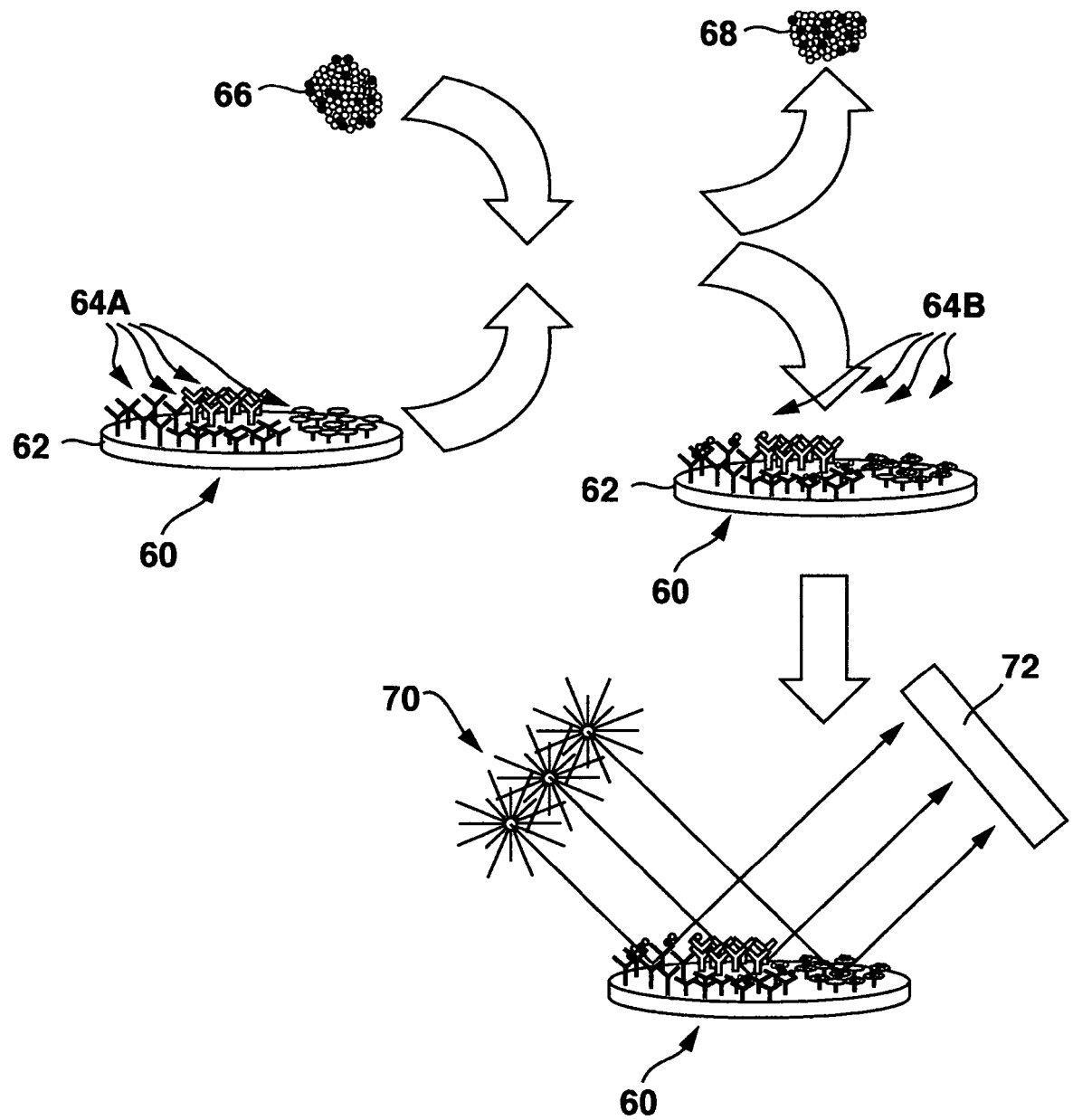
FIG. 5 is a conceptual diagram illustrating a technique for mass spectral analysis of a sample for biochemical markers.

FIG. 5 is a conceptual diagram illustrating a technique for measuring a plurality of biological markers. A biochip 60 comprises a substrate 62 and one or more sensing elements 64A. In FIG. 5, four distinct sensing elements are coupled to substrate 62, but the invention encompasses use of any number of sensing elements.

Biochip 60 is a set of miniaturized test sites, or microarrays, arranged on a solid substrate 62 made from a material such as silicone or glass. Each test site includes a set of sensing elements 64A. In general, sensing elements include one or more components that change conformation in the presence of an analyte of interest. Typical sensing elements include antibody molecules that change conformation in the presence of a specific biomarker but that do not change conformation in the presence of any other biomarker. The invention encompasses any sensing element, however, and is not restricted to antibodies. The sensing elements of biochip 60 may have general properties such as high affinity toward hydrophilic or hydrophobic molecules, or anionic or cationic proteins, for example.

Substrate 62 may have a surface area of about one square centimeter, but the invention encompasses biochips that are larger or smaller. Substrate 62 may be formed in any shape, may include any number of test sites, and may include any combination of sensing elements. The invention is not limited to any particular biochip.

Biochip 60 is exposed to sample 66. Sample 66 may include any biological sample from a patient, such as a blood sample. Biomarkers present in sample 66 react with sensing elements on biochip 60. Exposed sensing elements 64B typically react with biomarkers in sample 66 by undergoing a conformational change, or by forming ionic, covalent or hydrogen bonds. The unreacted or unbound portion of sample 68 is washed away.

The concentrations of biomarkers in sample 66 are a function of the extent of the reaction between exposed sensing elements 64 and sample 66. The extent of the reaction is determinable by, for example, mass spectrometry. The Surface Enhanced Laser Desorption/Ionization (SELDI) process is an example of a mass spectrometry technique for determining the concentrations of biomarkers that does not necessarily need antibodies. Instead, the molecules are absorbed onto a surface, and later released from the same surface with its energy absorbing matrix upon the application of external energy, usually in the form of light.

In general, the SELDI process directs light generated by one or more light sources 70 at biochip 60. A mass analyzer 72 measures the molecular weight of the biomarkers. In particular, biomarkers on biochip 60 are ionized and separated, and molecular ions are measured according to their mass-to-charge ratio (m/z). Ions are generated in the ionization source by inducing either the loss or the gain of a charge (e.g. electron ejection, protonation, or deprotonation). Once the ions are formed in the gas phase they can be electrostatically directed into mass analyzer 72, separated according to their mass and finally detected.

Proteins bound to sensing elements 64B, for example, can be ionized and separated based on molecular properties, such as being hydrophilic versus hydrophobic. Proteins captured by sensing elements 64B are freed by the energy provided by a weak laser pulse, and charged positively by the removal of a second electron as a result of illumination by a second laser pulse. Time of flight though a vacuum tube following acceleration in an electric field allows the measurement of the mass-to-charge ratio.

The invention supports other techniques for determining the concentrations of biomarkers, and is not limited to the SELDI process. In one embodiment, for example, the techniques of the invention could be carried out by using conventional assays for individual biomarkers, such as an Enzyme Linked ImmunoSorbent Assay (ELISA tests). An advantage of using a biochip is that a biochip saves time and effort in comparison to individual assays when multiple markers are to be measured.

Many protein markers are generally accepted as being indicative of cardiac conditions. C-Reactive Protein (CRP) is associated with sudden cardiac death, Fatty Acid Binding Protein is a plasma marker associated with acute myocardial infarction, Cardiac Troponin is associated with myocardial infarction, Myosin Light and Heavy Chains are associated with heart failure, brain natriuretic peptide (BNP) is associated with left ventricular heart failure, and so on.

Other markers may be associated with other cardiac conditions of interest. The markers may be identified by their name, or by other characteristics, such as molecular weight.

In an example clinical study, patients with coronary artery disease were divided into two groups: a test group that had coronary artery disease, and an implantable medical device (IMD) (with one sustained VT/VF episode with cycle length less than or equal to 400 ms); and a control group having coronary artery disease but no IMD, and no known history of VT/VF. In the study, sixteen patients had an IMD and thirty-two were in the control group. Certain patients were excluded from the study, including non-Caucasians, females, patients outside of age limit of 45-80, and patients having certain health problems or cardiac conditions. Patients meeting the inclusion criteria were enrolled in the study. Upon enrollment, an extensive questionnaire, including medical history was filled.

Three blood samples were drawn from each patient. At least one sample comprised 8.5 mL blood drawn from the patients for serum separation. Serum is the cell free portion of the blood containing proteins and lipids. At least one other sample of an additional 12 mL blood was drawn and kept as whole blood for eventual genetic analysis. The samples were analyzed using proteomic and lipidomic techniques.

During processing, proteins in the serum were fractionated into 4 distinct groups based on the pH (acidity) of the protein. Later on, these proteins were spotted onto three surfaces of one or more biochips. The surfaces had different chemical affinities. A surface designated "CM10" was responsive to weak cation exchange surface. A surface designated "H50" was a hydrophobic surface. A surface designated "IMAC" was an immobilized metal affinity surface. The SELDI time-of-flight technique was used to measure the molecular weight of the proteins on each surface.

Figure 6:
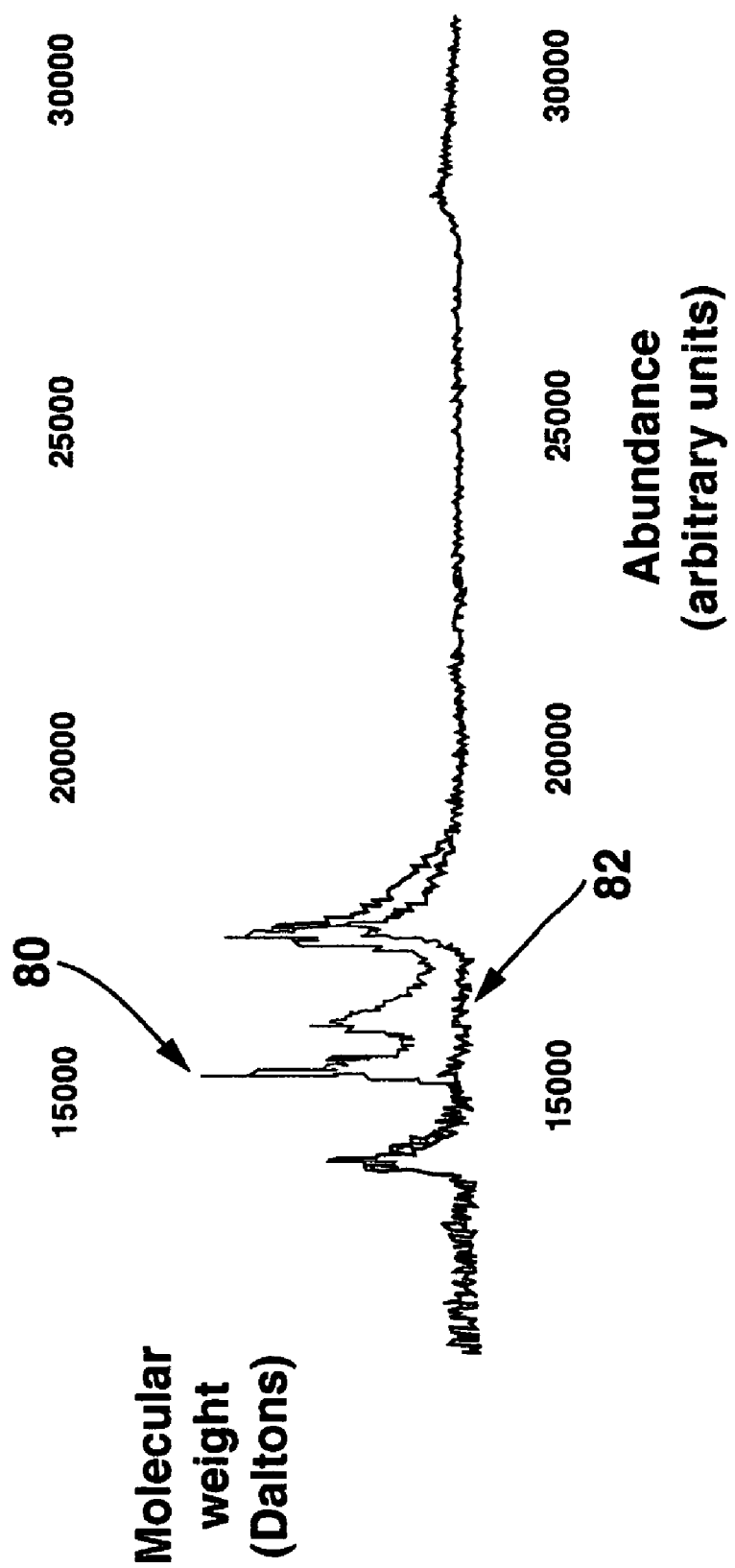
FIG. 6 is a graph showing differences in biochemical marker abundance for a patient at risk of ventricular tachyarrhythmia, compared to a patient in a control group.

FIG. 6 shows the results of sample proteomic spectra of two patients, one having an IMD (80) and one in the control (82). These results indicate that some of the protein markers in the blood were expressed differently in two groups. Data produced by processing of all of patients followed similar patterns, i.e., the data indicated that some of the protein markers in the blood obtained from patients were expressed differently in two groups. The differences in markers may form a basis for distinguishing the patients that would benefit from an IMD from the patients that would not benefit.

Figure 7:
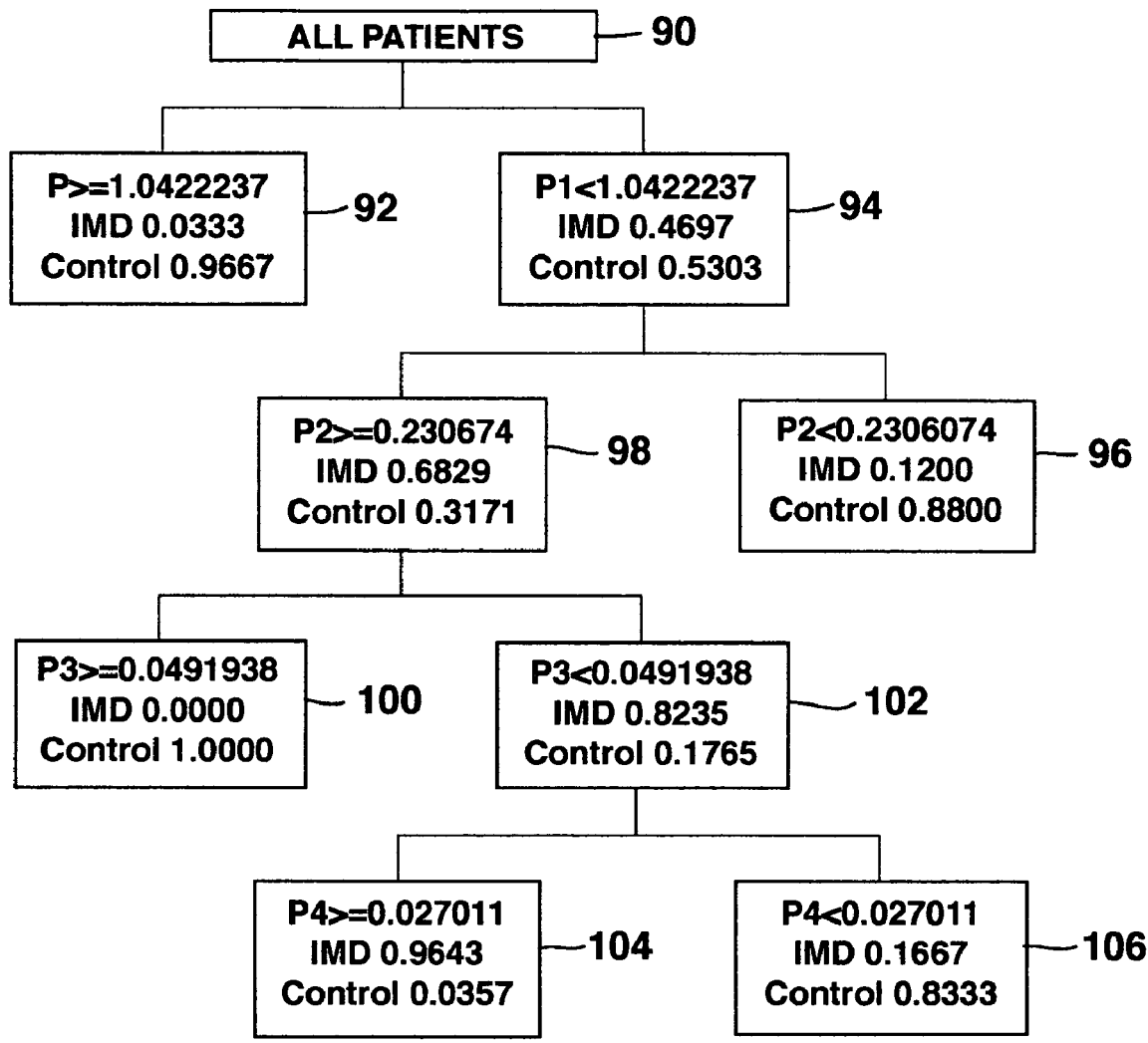
FIG. 7 is a logical diagram illustrating a technique for sorting patients at risk of ventricular tachyarrhythmia from a control group.

FIG. 7 shows a tree analysis applied to these results to identify potential biomarkers that differentiate patients who have a higher propensity for fatal ventricular arrhythmias from the others. As a result of the tree analysis, four protein markers could be used to classify the 48 patients correctly. Specifics of these protein markers are shown in the table below:

| Protein Number | Molecular Weight (Da) | Isoelectric pH (pI) | Capture Surface |
| --- | --- | --- | --- |
| P1 | 10,146.5 | 9+ | CM10 weak cation exchange) |
| P2 | 15,006 | 9+ | CM10 weak cation exchange) |
| P3 | 166,582 | 5–7 | CM10 weak cation exchange) |
| P4 | 10,948 | 9+ | IMAC (Immobilized Ion Affinity Surface) |

In the above table, proteins are identified by a number and are characterized by a molecular weight in Daltons and an Isoelectric pH (pI). The molecular weight in Daltons is not necessarily unique to any particular protein, but proteins are often distinguishable by molecular weight. It is not necessary to the invention that the protein having that molecular weight and/or pI be specifically identified by name or by amino-acid sequence.

As shown in FIG. 7, the amount of protein P1 in the serum was tested for all patients 90. Patients 92 having an abundance of P1 greater than or equal to 1.0422237 (measured in arbitrary units) were not at significant risk of ventricular tachyarrhythmia were therefore not candidates for an IMD. Patients 94 having an abundance of P1 less than 1.0422237, however, could not be classified by abundance of P1 alone.

For patients 94, the amount of protein P2 in the serum was tested. Patients 96 having an abundance of P2 less than 0.2306074 were not candidates for an IMD. Patients 98 having an abundance of P2 greater than or equal to 0.2306074 were tested for protein P3. Patients 100 having an abundance of P3 greater than or equal to 0.0491938 were not candidates for an IMD, while patients 102 having an abundance of P3 less than 0.0491938 were tested for protein P4. Patients 104 having an abundance of P4 greater than 0.027011 were considered to be candidates for an IMD, while the remaining patients 106 were not considered to be candidates for an IMD.

The arbitrary units may be normalized to an abundant protein, such as albumin, which is generally consistent in relative abundance among a group of patients or by spiking the original sample with a known concentration of an exogenous substance, and scaling the entire spectrum such that the measured value of the exogenous compound matches the amount that was added to the sample. The invention supports the use of other benchmarks as well, such as the total ion current in the mass spectrometer used to measure the protein abundance.

In addition, the invention supports a range of measurement standards. In some cases, it is not feasible to perform measurements that have one hundred percent sensitivity and specificity, and some standards may be applied to determine whether a patient is at significant risk of ventricular tachyarrhythmia or not. The tree analysis depicted in FIG. 7, for example, is generally more sensitive and specific than conventional patient sorting techniques (such as a signal averaged electrocardiogram), even though it may result in some false positives and false negatives.

The tree shown in FIG. 7 may be generated using Classification and Regression Tree (CART) analysis. The tree analysis depicted in FIG. 7 is an example of an approach for assessing a risk of ventricular tachyarrhythmia in one or more patients as a function of a measurement of one or more biochemical markers. The assessment may be performed in other ways as well. The test may be expressed as logical test such as an IF-THEN test, which can be implemented in software:

IF
    ((P1<1.0422237) AND (P2≧0.2306074) AND (P3<0.0491928) AND (P4≧0.027011))
THEN
    PATIENT IS AN IMD CANDIDATE

This IF-THEN test gave the following results when applied to the clinical data where two samples from each patient were processed:

|         | VT/VF | NORMAL |
|---------|-------|--------|
| TEST (+) | 27    | 1      |
| TEST (−) | 5     | 63     |

Sensitivity: 27/(27 + 5) = 84%
Specificity: 63/(63 + 1) = 98%
False Positives: 1/(1 + 27) = 4%
False Negatives: 5/(5 + 63) = 7%

Using conventional sorting techniques, sensitivity and specificity tend to be around 55 to 75 percent. This clinical data demonstrates an improvement in sensitivity and specificity in comparison to conventional techniques.

Another technique for assessing a risk of ventricular tachyarrhythmia in one or more patients as a function of a measurement of one or more biochemical markers is to use an artificial neural network. In an exemplary application, the clinical data were analyzed using an artificial neural network having four input nodes corresponding to proteins P1, P2, P3 and P4. The network included four hidden nodes and one output. This artificial neural network gave the following results when applied to the clinical data where two samples from each patient was processed:

|         | VT/VF | NORMAL |
|---------|-------|--------|
| TEST (+) | 24    | 1      |
| TEST (−) | 8     | 63     |

Sensitivity: 24/(24 + 8) = 75%
Specificity: 63/(63 + 1) = 98%
False Positives: 1/(1 + 25) = 4%
False Negatives: 8/(8 + 63) = 11%

A second representative clinical study to discover class identifiers was carried out with an additional 30 patients. These additional patients also had coronary artery disease and met specific inclusion criteria. They were divided into the two groups based on whether or not patients had an IMD. The patients having an IMD also had at least one true VTNF episode with a cycle length less than or equal to 400 ms terminated in the last 90 days. A total of 29 patients were in the test group, which consists of patients with an IMD, and 49 patients were in the control group.

Patients filled out an extensive questionnaire that included medical information that was then used in creating specimen/patient profiles. The following table shows the patient characteristics included the specimen profile and the relative breakdown between the test and control groups.

| Patient Characteristics | Patients in ICD Arm (N = 29) | Patients in Control Arm (N = 49) | Total Patients (N = 78) |
|---|---|---|---|
| Gender (N, %) | | | |
| Male | 29 (100%) | 49 (100%) | 78 (100%) |
| Female | 0 (0%) | 0 (0%) | 0 (0%) |
| Age (years) | | | |
| Mean | 68.8 | 67.1 | 67.8 |
| Standard Deviation | 8.2 | 8.1 | 8.1 |
| Minimum–Maximum Left Ventricular Ejection Fraction | 50–81 | 51–81 | 50–81 |
| Time since most recent LVEF (days) | | | |
| Mean | 1.1 | 0.9 | 1 |
| Standard Deviation | 1.1 | 1.1 | 1.1 |
| Minimum–Maximum | 0–5.3 | 0–4.8 | 0–5.3 |
| Most Recent Documented Measurement (%) | | | |
| Mean | 37.9 | 51.2 | 46.2 |
| Standard Deviation | 9.6 | 9.5 | 11.5 |
| Minimum–Maximum | 28–66 | 29–73 | 28–73 |
| Method of LVEF measurement | | | |
| Radionuclide angiocardiography/MUGA | 6 (21%) | 19 (39%) | 25 (32%) |
| Echo | 9 (31%) | 16 (33%) | 25 (32%) |
| Cath | 13 (45%) | 14 (29%) | 27 (35%) |
| Unknown | 0 (0%) | 0 (0%) | 0 (0%) |

The next table shows patient cardiovascular surgical and medical history that was included in the specimen profiles and the relative breakdown between the control and test groups.

| Patient Characteristics | Patients in ICD Arm (N = 29) | Patients in Control Arm (N = 49) | Total Patients (N = 78) |
|---|---|---|---|
| Cardiovascular Surgical History (N, %) | | | |
| None | 6 (20.7%) | 4 (8.2%) | 10 (12.8%) |
| Coronary Artery Bypass Graft | 14 (48.3%) | 20 (40.8%) | 34 (43.6%) |
| Coronary Artery Intervention | 13 (44.8%) | 36 (73.5%) | 49 (62.8%) |
| Angioplasty | 8 (27.6%) | 25 (51%) | 33 (42.3%) |
| Stent | 7 (24.1%) | 31 (63.3%) | 38 (48.7%) |
| Atherectomy | 0 (0%) | 0 (0%) | 0 (0%) |
| Ablation | 3 (10.3%) | 3 (6.1%) | 6 (7.7%) |
| Valvular Surgery | 1 (3.4%) | 1 (2%) | 2 (2.6%) |
| Other | 1 (3.4%) | 2 (4.1%) | 3 (3.8%) |
| Cardiovascular Medical History | | | |
| None | 0 (0%) | 0 (0%) | 0 (0%) |
| Coronary Artery Disease | 29 (100%) | 49 (100%) | 78 (100%) |
| Myocardial Infarction | 29 (100%) | 49 (100%) | 78 (100%) |
| Number of infarotions | | | |
| Mean | 1.4 | 1.3 | 1.3 |
| Standard Deviation | 0.6 | 0.5 | 0.5 |
| Minimum–Maximum | 1–3 | 1–3 | 1–3 |
| Time Since First Infarction (years) | | | |
| Mean | 10.2 | 6.6 | 7.9 |
| Standard Deviation | 7.7 | 5.6 | 6.6 |
| Minimum–Maximum | 1–26 | 0–22 | 0–26 |
| Time Since Most Recent Infarction (years) | | | |
| Mean | 5.3 | 5 | 5.1 |
| Standard Deviation | 5 | 5.4 | 5.2 |
| Minimum–Maximum | 1–17 | 0–22 | 0–22 |
| Hypertension | 19 (65.5%) | 34 (69.4%) | 53 (67.9%) |
| Cardiomyopathy | 18 (62.1%) | 3 (6.1%) | 21 (26.9%) |

-continued

| Patient Characteristics | Patients in ICD Arm (N = 29) | Patients in Control Arm (N = 49) | Total Patients (N = 78) |
|---|---|---|---|
| Hypertrophic | 5 (17.2%) | 0 (0%) | 5 (6.4%) |
| Dilated | 9 (31%) | 3 (6.1%) | 12 (15.4%) |
| Valve Disease/Disorder | 4 (13.8%) | 8 (16.3%) | 12 (15.4%) |
| Aortic | 0 (0%) | 5 (10.2%) | 5 (6.4%) |
| Tricuspid | 1 (3.4%) | 1 (2%) | 2 (2.6%) |
| Mitral | 4 (13.8%) | 3 (6.1%) | 7 (9%) |
| Pulmonary | 0 (0%) | 0 (0%) | 0 (0%) |
| Primary/Idiopathic Electrical Conduction Disease | 0 (0%) | 1 (2%) | 1 (1.3%) |
| Documented Accessory Pathway | 0 (0%) | 0 (0%) | 0 (0%) |
| Chronotropic Incompetence NYHA Classification | 1 (3.4%) | 0 (0%) | 1 (1.3%) |
| Class I | 4 (13.8%) | 3 (6.1%) | 7 (9%) |
| Class II | 6 (20.7%) | 5 (10.2%) | 11 (14.1%) |
| Class III | 4 (13.8%) | 0 (0%) | 4 (5.1%) |
| Class IV | 0 (0%) | 0 (0%) | 0 (0%) |
| Not Classified | 15 (51.7%) | 41 (83.7%) | 56 (71.8%) |
| Congenital Heart Disease | 0 (0%) | 0 (0%) | 0 (0%) |
| Other | 2 (6.9%) | 3 (6.1%) | 5 (6.4%) |

The table that follows shows patient arrhythmia history that was included in the specimen profiles and the relative breakdown between the control and test groups.

| Patient Characteristics | Patients in ICD Arm (N = 29) | Patients in Control Arm (N = 49) | Total Patients (N = 78) |
|---|---|---|---|
| Spontaneous Arrhythmia History (N, %) | | | |
| None | 0 (0%) | 26 (53.1%) | 26 (33.3%) |
| Ventricular | | | |
| Sustained Monomorphic VT | 23 (79.3%) | 0 (0%) | 23 (29.5%) |
| Sustained Polymorphic VT | 1 (3.4%) | 0 (0%) | 1 (1.3%) |
| Nonsustained VT | 17 (58.6%) | 0 (0%) | 17 (21.8%) |
| Ventricular Flutter | 1 (3.4%) | 0 (0%) | 1 (1.3%) |
| Ventricular Fibrillation | 9 (31%) | 0 (0%) | 9 (11.5%) |
| Torsades de Pointes | 0 (0%) | 0 (0%) | 0 (0%) |
| Long Q/T Syndrome | 0 (0%) | 0 (0%) | 0 (0%) |
| Other | 0 (0%) | 2 (4.1%) | 2 (2.6%) |
| Bradyarrythmias/ Conduction Disturbances | | | |
| Sinus Bradycardia | 5 (17.2%) | 14 (28.6%) | 19 (24.4%) |
| Sick Sinus Syndrome | 0 (0%) | 2 (4.1%) | 2 (2.6%) |
| 1° AV Block | 7 (24.1%) | 6 (12.2%) | 13 (16.7%) |
| 2° AV Block | 0 (0%) | 0 (0%) | 0 (0%) |
| Type I (Mobitz) | 0 (0%) | 0 (0%) | 0 (0%) |
| Type II (Wenckebach) | 0 (0%) | 0 (0%) | 0 (0%) |
| 3° AV Block | 0 (0%) | 0 (0%) | 0 (0%) |
| Right Bundle Branch Block | 5 (17.2%) | 8 (16.3%) | 13 (16.7%) |
| Left Bundle Branch Block | 4 (13.8%) | 2 (4.1%) | 6 (7.7%) |
| Bradycardia-Tachycardia Syndrome | 0 (0%) | 0 (0%) | 0 (0%) |
| Other | 2 (6.9%) | 0 (0%) | 2 (2.6%) |
| Atrial Arrythmia History (N, %) | | | |
| None | 14 (48.3%) | 36 (73.5%) | 50 (64.1%) |
| Atrial Tachycardia | 4 (13.8%) | 0 (0%) | 4 (5.1%) |
| Paroxysmal | 4 (13.8%) | 0 (0%) | 4 (5.1%) |
| Recurrent | 0 (0%) | 0 (0%) | 0 (0%) |
| Chronic | 0 (0%) | 0 (0%) | 0 (0%) |
| Atrial Flutter | 1 (3.4%) | 5 (10.2%) | 6 (7.7%) |
| Paroxysmal | 1 (3.4%) | 4 (8.2%) | 5 (6.4%) |
| Recurrent | 0 (0%) | 1 (2%) | 1 (1.3%) |
| Chronic | 0 (0%) | 0 (0%) | 0 (0%) |
| Atrial Fibrillation | 11 (37.9%) | 9 (18.4%) | 20 (25.6%) |
| Paroxysmal | 8 (27.6%) | 3 (6.1%) | 11 (14.1%) |
| Recurrent | 0 (0%) | 4 (8.2%) | 4 (5.1%) |
| Chronic | 3 (10.3%) | 1 (2%) | 4 (5.1%) |

The next table shows patient family history that was included in the specimen profiles and the relative breakdown between the control and test groups.

| Patient Characteristics | Patients in ICD Arm (N = 29) | Patients in Control Arm (N = 49) | Total Patients (N = 78) |
|---|---|---|---|
| Patient Family History (N, %) | | | |
| None | 20 (69%) | 31 (63.3%) | 51 (65.4%) |
| Long Q/T Syndrome | 0 (0%) | 0 (0%) | 0 (0%) |
| Grandparent | 0 (0%) | 0 (0%) | 0 (0%) |
| Parent | 0 (0%) | 0 (0%) | 0 (0%) |
| Sibling | 0 (0%) | 0 (0%) | 0 (0%) |
| Cousin | 0 (0%) | 0 (0%) | 0 (0%) |
| Sudden Cardiac Death | 5 (17.2%) | 11 (22.4%) | 16 (20.5%) |
| Grandparent | 0 (0%) | 1 (2%) | 1 (1.3%) |
| Parent | 4 (13.8%) | 8 (16.3%) | 12 (15.4%) |
| Sibling | 1 (3.4%) | 3 (6.1%) | 4 (5.1%) |
| Cousin | 0 (0%) | 1 (2%) | 1 (1.3%) |
| Sudden Death | 3 (10.3%) | 4 (8.2%) | 7 (9%) |
| Grandparent | 0 (0%) | 0 (0%) | 0 (0%) |
| Parent | 3 (10.3%) | 3 (6.1%) | 6 (7.7%) |
| Sibling | 1 (3.4%) | 1 (2%) | 2 (2.6%) |
| Cousin | 0 (0%) | 0 (0%) | 0 (0%) |
| Syncope | 2 (6.9%) | 1 (2%) | 3 (3.8%) |
| Grandparent | 0 (0%) | 0 (0%) | 0 (0%) |
| Parent | 2 (6.9%) | 0 (0%) | 2 (2.6%) |
| Sibling | 0 (0%) | 1 (2%) | 1 (1.3%) |
| Cousin | 0 (0%) | 0 (0%) | 0 (0%) |
| Deafness | 1 (3.4%) | 4 (8.2%) | 5 (6.4%) |
| Grandparent | 0 (0%) | 1 (2%) | 1 (1.3%) |
| Parent | 1 (3.4%) | 2 (4.1%) | 3 (3.8%) |
| Sibling | 0 (0%) | 1 (2%) | 1 (1.3%) |
| Cousin | 0 (0%) | 0 (0%) | 0 (0%) |
| History of Thrombo-embolic Event | | | |
| No | 24 (82.8%) | 44 (89.8%) | 68 (87.2%) |
| Yes | 5 (17.2%) | 5 (10.2%) | 10 (12.8%) |
| Time since most recent event (years) | | | |
| Mean | 1.8 | 4.2 | 3.2 |
| Standard Deviation | 1.4 | 6.3 | 4.7 |
| Minimum–Maximum | 0.8–3.4 | 0.2–13.5 | 0.2–13.5 |
| Type | | | |
| TIA | 2 (6.9%) | 1 (2%) | 3 (3.8%) |
| CVA | 2 (6.9%) | 1 (2%) | 3 (3.8%) |
| PE | 0 (0%) | 1 (2%) | 1 (1.3%) |
| Renal | 0 (0%) | 0 (0%) | 0 (0%) |
| Peripheral | 0 (0%) | 0 (0%) | 0 (0%) |
| Other | 1 (3.4%) | 2 (4.1%) | 3 (3.8%) |
| Other History | | | |
| History of Hyperthyroidism | 0 (0%) | 2 (4.1%) | 2 (2.6%) |
| Hearing loss | 12 (41.4%) | 16 (32.7%) | 28 (35.9%) |

The table below shows patient lifestyle characteristics that were included in the specimen profiles and the relative breakdown between the control and test groups.

| Patient Characteristics | Patients in ICD Arm (N = 29) | Patients in Control Arm (N = 49) | Total Patients (N = 78) |
|---|---|---|---|
| Does the Patient Smoke? | | | |
| No | 23 (79.3%) | 42 (85.7%) | 65 (83.3%) |
| Yes | 6 (20.7%) | 7 (14.3%) | 13 (16.7%) |
| Number of Years | | | |
| Mean | 41.6 | 39.6 | 40.4 |
| Standard Deviation | 11.1 | 8 | 9 |
| Minimum–Maximum | 30–55 | 30–50 | 30–55 |
| Degree of Smoking | | | |
| 1–2 packs a week | 1 (3.4%) | 2 (4.1%) | 3 (3.8%) |
| 3–5 packs a week | 0 (0%) | 1 (2%) | 1 (1.3%) |
| 5–10 packs a week | 2 (6.9%) | 3 (6.1%) | 5 (6.4%) |
| 10 or more packs a week | 1 (3.4%) | 0 (0%) | 1 (1.3%) |
| Use of Alcohol | | | |
| No | 17 (58.6%) | 24 (49%) | 41 (52.6%) |
| Yes | 12 (41.4%) | 25 (51%) | 37 (47.4%) |
| Number of Years | | | |
| Mean | 36.7 | 38.2 | 37.7 |
| Standard Deviation | 17 | 13.9 | 14.7 |
| Minimum–Maximum | 10–59 | 4–60 | 4–60 |
| Degree of Drinking | | | |
| 1–2 drinks a week | 5 (17.2%) | 6 (12.2%) | 11 (14.1%) |
| 3–5 drinks a week | 1 (3.4%) | 7 (14.3%) | 8 (10.3%) |
| 5–10 drinks a week | 4 (13.8%) | 6 (12.2%) | 10 (12.8%) |
| 10 or more drinks a week | 2 (6.9%) | 5 (10.2%) | 7 (9%) |

The following table shows patient baseline medications that were included in the specimen profiles and the relative breakdown between the control and test groups.

| Patient Medications | Patients in ICD Arm (N = 29) | Patients in Control Arm (N = 49) | Total Patients (N = 78) |
|---|---|---|---|
| Any Medications in Prior 6 Months (N, %) | | | |
| No | 0 (0%) | 0 (0%) | 0 (0%) |
| Yes | 29 (100%) | 49 (100%) | 78 (100%) |
| Class I | 4 (13.8%) | 1 (2%) | 5 (6.4%) |
| Disopyramide | 0 (0%) | 0 (0%) | 0 (0%) |
| Flecainide | 0 (0%) | 0 (0%) | 0 (0%) |
| Mexiletine | 1 (3.4%) | 0 (0%) | 1 (1.3%) |
| Moricizine | 0 (0%) | 0 (0%) | 0 (0%) |
| Procainamide | 2 (6.9%) | 0 (0%) | 2 (2.6%) |
| Propafenone | 0 (0%) | 1 (2%) | 1 (1.3%) |
| Quinidine | 1 (3.4%) | 0 (0%) | 1 (1.3%) |
| Tocainide | 0 (0%) | 0 (0%) | 0 (0%) |
| Other | 0 (0%) | 0 (0%) | 0 (0%) |
| Class III | 14 (48.3%) | 4 (8.2%) | 18 (23.1%) |
| Amiodarone | 8 (27.6%) | 2 (4.1%) | 10 (12.8%) |
| Dofetilide | 0 (0%) | 0 (0%) | 0 (0%) |
| Sotalol | 7 (24.1%) | 2 (4.1%) | 9 (11.5%) |
| Other | 0 (0%) | 0 (0%) | 0 (0%) |
| Beta Blockers | 17 (58.6%) | 36 (73.5%) | 53 (67.9%) |
| Atenolol | 1 (3.4%) | 9 (18.4%) | 10 (12.8%) |
| Betaxolol | 0 (0%) | 0 (0%) | 0 (0%) |
| Bisoprolol | 0 (0%) | 0 (0%) | 0 (0%) |
| Bucindolol | 0 (0%) | 0 (0%) | 0 (0%) |
| Carvedilol | 4 (13.8%) | 3 (6.1%) | 7 (9%) |
| Metoprolol | 11 (37.9%) | 22 (44.9%) | 33 (42.3%) |
| Nadolol | 0 (0%) | 0 (0%) | 0 (0%) |
| Penbutolol | 0 (0%) | 0 (0%) | 0 (0%) |
| Propranolol | 1 (3.4%) | 2 (4.1%) | 3 (3.8%) |
| Timolol | 0 (0%) | 0 (0%) | 0 (0%) |
| Other | 0 (0%) | 1 (2%) | 1 (1.3%) |
| Calcium Channel Blockers | 4 (13.8%) | 10 (20.4%) | 14 (17.9%) |
| Amlodipine | 2 (6.9%) | 4 (8.2%) | 6 (7.7%) |
| Diltiazem | 0 (0%) | 3 (6.1%) | 3 (3.8%) |
| Ibepridil | 0 (0%) | 0 (0%) | 0 (0%) |
| Felodipine | 0 (0%) | 0 (0%) | 0 (0%) |
| Nifedipine | 0 (0%) | 3 (6.1%) | 3 (3.8%) |
| Nisoldipine | 0 (0%) | 0 (0%) | 0 (0%) |
| Nimodipine | 0 (0%) | 0 (0%) | 0 (0%) |
| Verapamil | 1 (3.4%) | 0 (0%) | 1 (1.3%) |
| Other | 1 (3.4%) | 0 (0%) | 1 (1.3%) |
| Digoxin | 9 (31%) | 3 (6.1%) | 12 (15.4%) |
| Anti-Coagulants | 28 (96.6%) | 46 (93.9%) | 74 (94.9%) |
| Warfarin | 5 (17.2%) | 8 (16.3%) | 13 (16.7%) |
| Aspirin | 25 (86.2%) | 40 (81.6%) | 65 (83.3%) |
| Other | 4 (13.8%) | 14 (28.6%) | 18 (23.1%) |
| Other | 26 (89.7%) | 39 (79.6%) | 65 (83.3%) |

Protein analysis from patient blood samples was carried out as described in the previous example. The CART (Classification and Regression Tree) method was used to identify class identifiers. The iterative partitioning algorithm used the test versus control groupings as the response variables and 2076 predictor variables that included 86 demographic variables and 1990 protein/peptide variables. Eligible protein/peptide variables were identified as peaks in spectral analyses of at least 4% of patients. Each patient's protein level for a given variable was averaged from two peak measurements.

Figure 8:
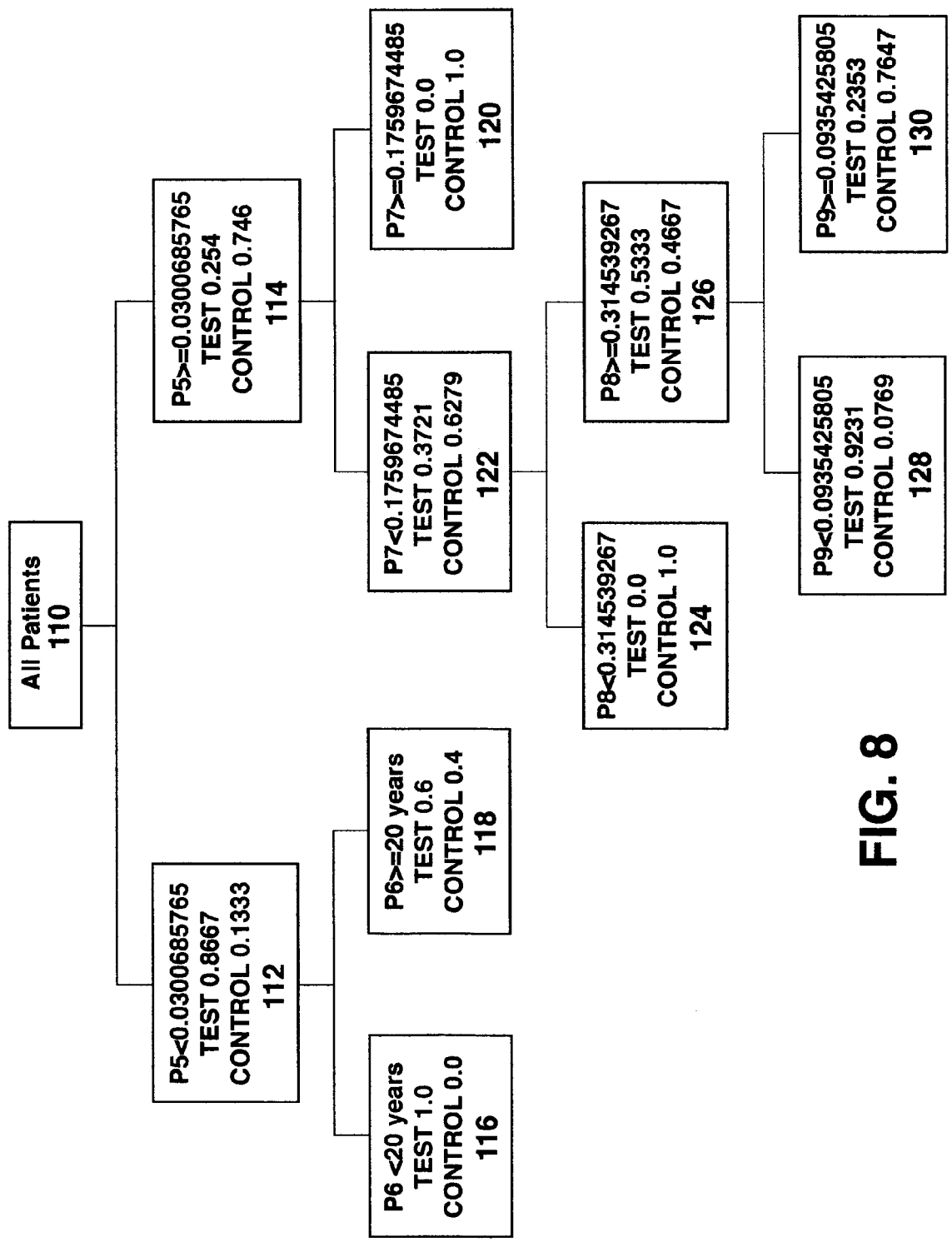
FIG. 8 is a logical diagram illustrating a technique for classifying patients at risk of ventricular tachyarrhythmia.

FIG. 8 is the resulting tree analysis from the CART analysis. Tree analysis 108 uses the five identified class identifiers, P5, P6, P7, P8, and P9, to classify all patients, represented as group 110, based on risk for fatal VT/VF.

The most effective class identifier is protein P5. Fifteen patients having P5 levels less than 0.0300685765 (measured in arbitrary units) were placed in group 112. Thirteen, or 86.7%, were test patients with IMDs. Sixty-three patients having P5 levels greater than or equal to 0.0300685765 were placed in group 114. Sixteen, or 25.4%, were test patients.

The class identifier shown to further partition group 112 and represented as P6 was consumption of alcohol or lack of consumption for less than 20 years. Ten patients (eight of which had never consumed alcohol) were placed in group 116. All 10 patients, or 100%, were test patients. Five patients that had consumed alcohol for more than 20 years were placed in group 118. Three of these five patients, or 60%, were test patients.

Group 114 was then further partitioned based on levels of protein P7. Twenty patients having P7 levels greater than or equal to 0.1759674485 were placed into group 120. All 20, or 100%, were control patients. Forty-three patients having P7 levels less than 0.1759674485 were placed into group 122. Twenty-seven of these 43 patients, or 62.8%, were control patients.

Group 122 was further partitioned based on levels of protein P8. Thirteen patients having P8 levels less than 0.314539267 were placed into group 124. All 13, or 100%, were control patients. Thirty patients having P8 levels greater than or equal to 0.314539267 were placed into group 126. Fourteen of these 30 patients, or 46.7%, were control patients.

Further partitioning of group 126 was based on levels of protein P9. Thirteen patients having P9 levels less than 0.0935425805 were placed into group 128. Twelve of these patients, or 92.3%, were test patients. Seventeen patients having P9 levels greater than or equal to 0.0935425805 were placed into group 130. Only four of these 17 patients, or 23.5%, were test patients.

Thus, when applying tree analysis 108, patients falling into groups 116 and 128 have a significant risk of experiencing VTNF and would benefit from an IMD. Conversely, patients falling into groups 120, 124, and 130 do not have a significant risk of experiencing VTNF.

The table below summarizes the percentage of test patients belonging to each group of tree analysis 108.

| P5 | P6 | P7 | P8 | P9 | Col. 6 | Col. 7* |
|---|---|---|---|---|---|---|
| <0.0300685765 | Subtotal | | | | 15 | 86.7 |
| | ≧20 years | | | | 5 | 60 |
| | <20 years | | | | 10 | 100 |
| ≧0.0300685765 | N/A | Subtotal | | | 63 | 25.4 |
| | | ≧0.1759674485 | | | 20 | 0 |
| | | <0.1759674485 | Subtotal | | 43 | 37.2 |
| | | | <0.314539267 | | 13 | 0 |
| | | | ≧0.314539267 | Subtotal | 30 | 53.3 |
| | | | | ≧0.0935425805 | 17 | 23.5 |
| | | | | <0.0935425805 | 13 | 92.3 |
| | | Total | | | 78 | 37.2 |

*Each percentage is for the applicable group of the corresponding row; therefore, the percentages do not sum to 100%, as they are calculated with different denominators (patient sample sizes).

Columns one through five represent the class identifiers, P5-P9 and rows represent groups 112-130 obtained by using the class identifiers. Column 6 (Col. 6) is the total number of patients belonging to each corresponding group, and column 7 (Col. 7) is percentage of patients in each group that are test patients.

For example, to assess the percentage of test patients among all patients having P5 levels greater than or equal to 0.0300685765 and P7 levels less than 0.1759674485, begin at column 1 and select the row corresponding to ≧0.0300685765. Move to columns 2 and 3 (column 2 does not apply to these patients) and select the row in column 3 corresponding to <0.1759674485. Moving across to column 6, the number of patients having these class identifiers is 43, and the corresponding row in column 7 indicates that 37.2% of the 43 patients were test patients.

The following table summarizes the information regarding proteins P5, P7, P8, and P9.

| Molecular Weight | Chip Type | Fraction of Isolation | Spectrum Range | Partitioning Peak Intensity |
|---|---|---|---|---|
| P5 11991 | Immobilized Metal Affinity Surface | Combined fractions f2 and f3 containing pH 5–7 | High Protein | 0.0300685765 |
| P7 10552.4 | Weak Cation Exchange Surface | Fraction 1 containing flow-through and pH = 9 | High Protein | 0.1759674485 |
| P8 43529.4 | Weak Cation Exchange Surface | Fraction 1 containing flow-through and pH = 9 | High Protein | 0.314539267 |
| P9 | Hydrophobic | Fraction 1 | Protein | 0.0935425805 |
| 13806.8 | Surface | containing flow-through and pH = 9 | | |

This analysis resulted in four protein class identifiers and one demographic class identifier that correctly classifies patients based on risk of experiencing a true VTNF episode.

The test procedures described above are not unique, nor are they necessarily the most efficient method of sorting patients who are candidates for an IMD from those that are not. Nevertheless, these procedures are illustrations of tests that can be used to screen patients to find out the ones who have a propensity for ventricular tachyarrhythmia, and thus may be at increased risk of sudden cardiac death.

Depending upon the biochemical markers of interest, measurements of mass, concentration or abundance may be less important than determination of whether the marker is present or absent. The invention encompasses embodiments in which measurement of a biochemical marker in a patient includes determining whether the marker is present or not. For example, animal experimentation may establish that animals suffering sudden cardiac death exhibit an absence of a set of proteins and peptides having particular molecular weights. Similarly, animal experimentation may establish that animals suffering sudden cardiac death exhibit proteins or peptides that are otherwise not present. Detection of the presence or absence of such proteins or peptides in a human sample may have clinical significance, as the presence or absence proteins or peptides may be indicative of risk of sudden cardiac death.

In some cases, what is of interest is not the presence or absence of a biochemical marker, or its concentration on a single occasion, but an increase or decrease in the concentration or the rate of change, as demonstrated by two or more measurements separated by a time interval such as two weeks or one month. The invention supports consideration of change as a basis for assessing a risk of ventricular tachyarrhythmia.

Figure 9:
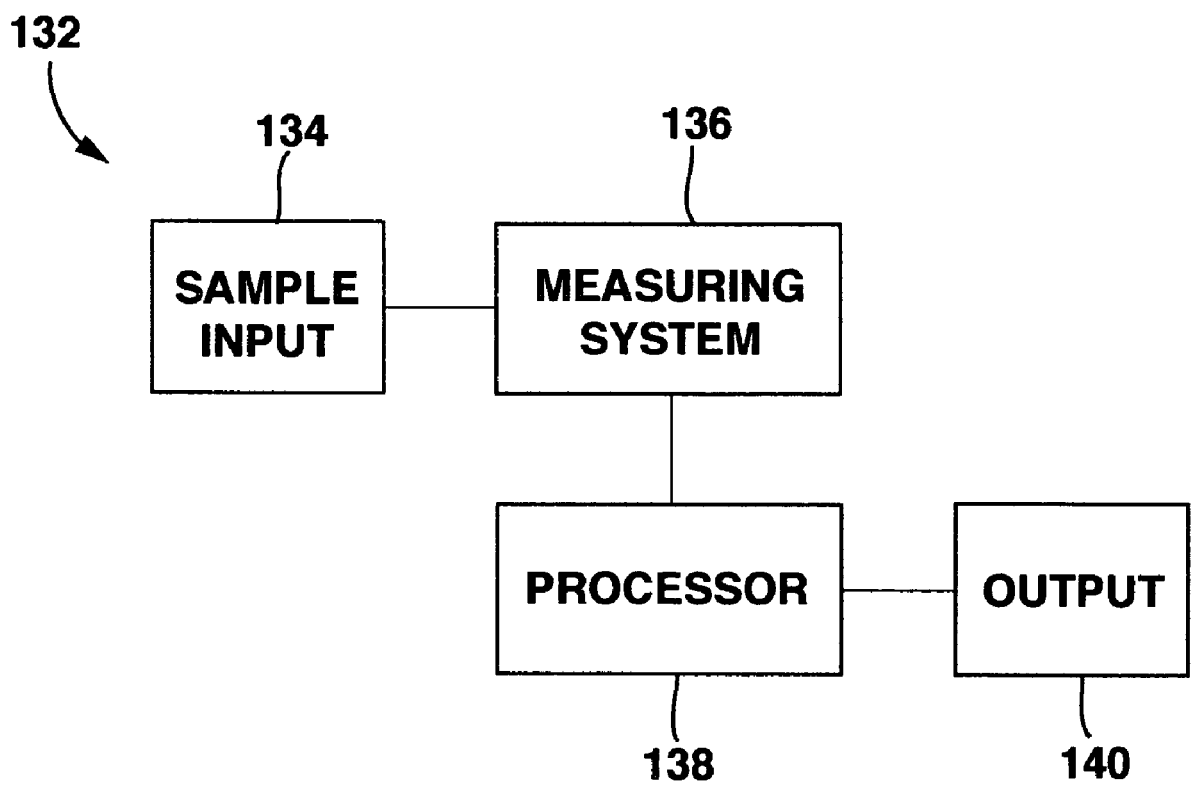
FIG. 9 is a block diagram of a system configured to carry out an embodiment of the invention.

Test procedures such as the exemplary procedures described above can be automated, in whole or in part. FIG. 9 is an example of a system 132 that can perform an automated analysis of biochemical markers and can assess a risk of ventricular tachyarrhythmia in a patient as a function of the analysis. System 132 includes a sample input module 134, which receives a sample for analysis, and a measuring system 136. In one embodiment of the invention, input module 134 may include one or more biochips like those depicted in FIG. 5, and measuring system 136 may comprise a SELDI-based mass analyzer. The invention is not limited to such components, however.

A processor 138 receives the measurements from measuring system 136 and assessing a risk of ventricular tachyarrhythmia in the patient as a function by analyzing the measurements. Processor 138 may apply a tree analysis, such as the analyses depicted in FIGS. 1, 2, 7, and 8 to determine whether a patient is at risk of ventricular tachyarrhythmia. Processor 138 may further assess a benefit of implanting a medical device in the patient as a function of the measurements, or administering an antiarrhythmic drug to the patient.

An output module 140 reports the results of the analysis. Output module 140 may comprise a display screen, printer, or any other device that reports the results of the analysis. A benefit of implanting a medical device in the patient as a function of the measurement is assessed.

The invention may offer one or more advantages. Clinical data suggest that, in a significant number of cases, sudden cardiac death is the result of VT or VF. Episodes of VT or VF are treatable with an IMD or medication. The invention presents techniques for identifying the patients who are at risk of experiencing ventricular tachyarrhythmia. As a result, there is an improved chance that these patients will receive life-saving therapy, thereby reducing their risk of sudden cardiac death.

For example, recent evidence shows that VT/VF is treatable by administration of clonidine or vagal nerve stimulation, as well as through stimulation by an implantable cardioverter defibrillator (ICD). Thus, biomarkers may be used to identify patients that would benefit from these treatments and/or benefit from IMDs such as a drug pump to deliver intrathecal clonidine, a vagal nerve stimulator, or an ICD.

Therapies involving an IMD or medication need not be exclusive of one another. Furthermore, the invention supports therapies in addition to implantation of an IMD or regulation of a regimen of medication. In some circumstances, the biomarkers may be more than symptomatic or indicative of the risk of VT or VF, and may be substantially causally related to the risk of VT or VF. In such circumstances, therapy may be directed to the biomarkers.

It may be possible, for example, to treat the patient by adjusting the concentration of biomarkers. When a concentration of certain protein biomarkers is found to be lower in a patient with VT or VF, then perhaps the patient can be treated by injecting those proteins into the blood, thereby restoring a more healthful concentration of the biomarkers. Conversely, when a concentration of certain protein biomarkers is found to be higher, then perhaps the patient can be treated by reducing the concentration of the protein biomarkers. A high concentration can be reduced by, for example, injection of enzymes that cleave or inhibit the activity of one or more protein biomarkers. Similarly, gene therapy can be used to alter protein and gene expression levels. Consequently, application of therapy may include determining one or more proteins or one or more genes, or a combination thereof, to be delivered to the patient.

The techniques of the invention may call for sample from the patient. In many embodiments, the sample is one that is taken as a matter of course in a medical examination, such as a blood sample.

Further, the invention should reduce the incidents of false positives and false negatives. As a result, there is a better chance that patients that can benefit from an IMD will have a chance to receive an IMD. In addition, the invention includes the capability of being self-improving. As more clinical data are collected, different or more detailed tree analyses or other sorting techniques may be developed. Empirical experience may make tests more sensitive and more specific.

Various embodiments of the invention have been described. Various modifications can be made to the described embodiments without departing from the scope of the invention. For example, the invention is not limited to consideration of biochemical markers exclusively. The assessment of risk of ventricular tachyarrhythmia in the patient may also be a function of other measurable physiological factors. Electrophysiological measurements, such as an electrocardiogram, and hemodynamic factors, such as a measurement of ejection fraction, may be taken into consideration. Demographic factors such as number of CABG procedures as well as alcohol and tobacco use are also factors that may be included. System 110 in FIG. 9 may further include a sensor to measure a physiological factor, and processor 116 may assess a risk of ventricular tachyarrhythmia as a function of the measurement of the physiological factor.

Although the invention has been described with proteins as biochemical markers, the invention is not limited to proteins. The invention also supports consideration of other markers, such as genetic markers, lipid markers and lipoprotein markers. The markers may be considered alone or in combination. For example, the invention supports risk assessments as a function of combinations of gene and protein markers. Techniques such as nuclear magnetic resonance, gene sequencing, or single nucleotide polymorphism (SNP) may be used to identify these markers. Consideration of markers such as these may result in enhanced sensitivity and specificity.

Analysis can be done using multiple techniques. In addition to generating a sorting tree, applying a logical analysis such as an IF-THEN statement, and artificial neural networks, one can assess a risk of ventricular tachyarrhythmia using linear clustering techniques (e.g. proximity, similarity, dissimilarity, weighted proximity, and principle component analysis), non-linear clustering techniques (e.g. artificial neural networks, Kohonen networks, pattern recognizers and empirical curve fitting), as well as logical procedures (e.g. CART, partition and hierarchical clustering algorithms). The invention is not limited to these techniques, however, and encompasses other linear analysis, non-linear analysis, logical analysis and conditional techniques.

Some of the techniques described above may be embodied as a computer-readable medium comprising instructions for a programmable processor such as processor 138 in FIG. 9. The programmable processor may include one or more individual processors, which may act independently or in concert. A "computer-readable medium" includes but is not limited to read-only memory, Flash memory and a magnetic or optical storage medium.

Although the present invention has been described with reference to preferred embodiments, workers skilled in the art will recognize that changes may be made in form and detail without departing from the spirit and scope of the invention.

The invention claimed is:

1. A method of assessing a patient for risk of sudden cardiac death (SCD), the method comprising:
   determining an amount of at least one SCD-associated protein in the patient;
   assessing the risk as a function of the determination;

determining occurrence of at least one class identifier that assesses the patient as having increased risk of SCD;

combining results of the occurrence of the class identifier and the amount of SCD-associated protein;

wherein assessing the patient is based on the combined results; and wherein the SCD-associated protein is selected from a group of proteins having characteristics consisting of 10,146.5 Da and pI=9+; 15,006 Da and pI=9+; 166,582 Da and pI=5-7; 10,948 Da and pI=9+; 11,991 Da and pI=5-7; 10,552.4 Da and pI=9; 43,529.4 Da and pI=9; and 13,806.8 Da and pI=9.

2. The method of claim 1, wherein the at least one SCD-associated protein is identified by measuring a mass of the protein, measuring a mass-to-charge ratio of the protein with a mass spectrometer, and measuring an isoelectric pH (pI) of the protein.

3. The method of claim 1, wherein the amount of SCD-associated protein in the patient that indicates increased risk of SCD is one of higher and lower than an amount of SCD-associated protein in a patient having no increased risk of SCD.

4. The method of claim 1 wherein the SCD-associated protein is used as a therapeutic agent.

5. A method of identifying patients that would benefit from an implanted medical device, the method comprising:

identifying at least one SCD-associated protein;

determining an amount of SCD-associated protein from a protein-containing sample from a patient;

assessing whether the patient would benefit from an implanted medical device based on the amount of the SCD-associated protein wherein the implanted medical device is an electronic stimulation device; and wherein the SCD-associated protein is selected from a group of proteins having characteristics consisting of 10,146.5 Da and pI=9+; 15,006 Da and pI=9+; 166,582 Da and DI=5-7; 10,948 Da and pI=9+; 11,991 Da and pI=5-7; 10,552.4 Da and pI=9; 43,529.4 Da and pI=9; and 13,806.8 Da and pI=9.

6. The method of claim 5 wherein identifying at least one SCD-associated protein further comprises:

collecting protein-containing samples from patients having increased risk of SCD;

collecting protein-containing samples from patients having no increased risk of SCD;

identifying at least one protein from the protein-containing samples whose amount differs between patients having increased risk of SCD and patients having no increased risk of SCD; and wherein the identified proteins are SCD-associated proteins.

7. The method of claim 5 wherein assessing is achieved with an algorithm comprising determination of at least one SCD-associated protein selected from a group of proteins having characteristics consisting of 11,991 Da and pI=5-7; 10,552.4 Da and pI=9; 43,529.4 Da and pI=9; and 13,806.8 Da and pI=9.

8. The method of claim 7 wherein the algorithm further comprises determination of a class identifier associated with SCD.

9. A method of identifying a SCD-associated protein comprising:

collecting first protein-containing samples from patients having increased risk of SCD;

collecting second protein-containing samples from patients having no increased risk of SCD;

determining amounts of proteins in the first and second protein-containing samples; and identifying a protein having an amount that differs between the first and second protein-containing samples;

wherein the SCD-associated protein is selected from a group of proteins having characteristics consisting of 10,146.5 Da and pI=9+; 15,006 Da and pI=9+; 166,582 Da and pI=5-7; 10,948 Da and pI=9+; 11,991 Da and pI=5-7; 10,552.4 Da and pI=9; 43,529.4 Da and pI=9; and 13,806.8 Da and pI=9.

10. The method of claim 9, wherein the amount that differs between the first and second protein-containing samples comprises one of presence of the protein, absence of the protein, increased amount of the protein, decreased amount of the protein, and change of concentration of the protein over a time period.

11. The method of claim 9 wherein the identified protein is described by molecular weight and Isoelectric pH.

12. The method of claim 11 wherein the identified protein is further described by mass-to-charge ratio.

13. A method of assessing a patient for risk of sudden cardiac death (SCD), the method comprising: determining an amount of at least one SCD-associated protein in the patient; and assessing the risk based on the determined amount of SCD-associated protein wherein the SCD-associated protein is selected from a group of proteins having characteristics consisting of 10,146.5 Da and pI=9+; 15,006 Da and pI=9+; 166,582 Da and pI=5-7; 10,948 Da and pI=9+; 11,991 Da and pI=5-7; 10,552.4 Da and pI=9; 43,529.4 Da and pI=9; and 13,806.8 Da and pI=9.

14. The method of claim 13, wherein the at least one SCD-associated protein is identified by measuring a mass of the protein, measuring a mass-to-charge ratio of the protein with a mass spectrometer, and measuring an isoelectric pH (pI) of the protein.

15. The method of claim 13, wherein the amount of SCD-associated protein in the patient that indicates increased risk of SCD is one of higher and lower than an amount of SCD-associated protein in a patient having no increased risk of SCD.

16. The method of claim 13 wherein the SCD-associated protein is used as a therapeutic agent.

17. A method of identifying patients that would benefit from an implanted medical device, the method comprising:

identifying at least one SCD-associated protein;

determining an amount of SCD-associated protein from a protein-containing sample from a patient;

assessing whether the patient would benefit from an implanted medical device based on the amount of the SCD-associated protein, wherein the SCD-associated protein is selected from a group of proteins having characteristics consisting of 10,146.5 Da and pI=9+; 15,006 Da and pI=9+; 166,582 Da and pI=5-7; 10,948 Da and pI=9+; 11,991 Da and pI=5-7; 10,552.4 Da and pI=9; 43,529.4 Da and pI=9; and 13,806.8 Da and pI=9.

18. The method of claim 17 wherein identifying at least one SCD-associated protein further comprises:

collecting protein-containing samples from patients having increased risk of SCD;

collecting protein-containing samples from patients having no increased risk of SCD;

identifying at least one protein from the protein-containing samples whose amount differs between patients having increased risk of SCD and patients having no increased risk of SCD; and wherein the identified proteins are SCD-associated proteins.

19. The method of claim 17 wherein the implanted medical device comprises at least one of an electronic stimulation device and a drug delivery device.

20. The method of claim 17 wherein assessing is achieved with an algorithm comprising determination of at least one SCD-associated protein selected from a group of proteins having characteristics consisting of 11,991 Da and pI=5-7; 10,552.4 Da and pI=9; 43,529.4 Da and pI=9; and 13,806.8 Da and pI=9.

21. The method of claim 20 wherein the algorithm further comprises determination of a class identifier associated with SCD.

22. A method of assessing a patient for risk of sudden cardiac death (SCD), the method comprising:

determining the presence or absence of at least one SCD-associated protein in the patient;

assessing the risk as a function of the determination;

determining occurrence of at least one class identifier that assesses the patient as having increased risk of SCD;

combining results of the occurrence of the class identifier;

wherein assessing the patient is based on the combined results; and wherein the SCD-associated protein is selected from a group of proteins having characteristics consisting of 10,146.5 Da and pI=9+; 15,006 Da and pI=9+; 166,582 Da and pI=5-7; 10.948 Da and pI=9+; 11,991 Da and pI=5-7; 10,552.4 Da and pI=9; 43,529.4 Da and pI=9; and 13,806.8 Da and pI=9.

23. The method of claim 22, wherein the at least one SCD-associated protein is identified by measuring a mass of the protein, measuring a mass-to-charge ratio of the protein with a mass spectrometer, and measuring an isoelectric pH (pI) of the protein.

24. The method of claim 22, wherein the amount of SCD-associated protein in the patient that indicates increased risk of SCD is one of higher and lower than an amount of SCD-associated protein in a patient having no increased risk of SCD.

25. The method of claim 22 wherein the SCD-associated protein is used as a therapeutic agent.

* * * * *

UNITED STATES PATENT AND TRADEMARK OFFICE
CERTIFICATE OF CORRECTION

PATENT NO. : 7,608,458 B2  Page 1 of 1
APPLICATION NO. : 11/157549
DATED : October 27, 2009
INVENTOR(S) : Soykan et al.

It is certified that error appears in the above-identified patent and that said Letters Patent is hereby corrected as shown below:

In col. 5, lines 8-10 should read as follows: -- and a control group having coronary artery disease but no IMD, and no known history of ~~VTNF~~ VT/VF. --

In col. 6, lines 1-9 should read as follows: -- In the above table, proteins are identified by a number and are characterized by a molecular weight in Daltons and an Isoelectric pH (~~pI~~ pI). The molecular weight in Daltons is not necessarily unique to any particular protein, but proteins are often distinguishable by molecular weight. It is not necessary to the invention that the protein having that molecular weight and/or ~~pI~~ pI be specifically identified by name or by amino-acid sequence. --

In col. 13, lines 6-10 should read as follows: -- Thus, when applying a tree analysis 108, patients falling into groups 116 and 128 have a significant risk of experiencing ~~VTNF~~ VT/VF and would benefit from an IMD. Conversely, patients falling into groups 120, 124, and 130 do not have significant risk of experiencing ~~VTNF~~ VT/VF. --

In col. 14, lines 31-33 should read as follows: -- This analysis resulted in four protein class identifiers and one demographic class identifier that correctly classifies patients based on risk of experiencing a true ~~VTNF~~ VT/VF episode. --

In Claim 5, col. 17, lines 35-40 should read as follows: -- wherein the SCD-associated protein is selected from a group of proteins having characteristics consisting of 10,146.5 Da and pI=9+; 15,006 Da and pI=9+; 166,582 Da and ~~DI~~ pI=5-7; 10,948 Da and pI=9+; 11,991 Da and pI=5-7; 10,552.4 Da and pI=9; 43,529.4 Da and pI=9; and 13,806.8 Da and pI=9. --

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,608,458 B2 Page 1 of 1
APPLICATION NO. : 11/157549
DATED : October 27, 2009
INVENTOR(S) : Soykan et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 842 days Delete the phrase "by 842 days" and insert -- by 1153 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,608,458 B2  Page 1 of 1
APPLICATION NO. : 11/157549
DATED : October 27, 2009
INVENTOR(S) : Soykan et al.

It is certified that error appears in the above-identified patent and that said Letters Patent is hereby corrected as shown below:

Title page, item (*) Notice:   Subject to any disclaimer, the term of this patent is extended or adjusted under 35 U.S.C. 154(b) by 1153 days.

Delete the phrase "by 1153 days" and insert -- by 1464 days --.

Col. 17, Line 38,
Claim 5,            ...and DI = 5-7...     should be     ...and pl = 5-7...

Signed and Sealed this

Seventeenth Day of August, 2010

David J. Kappos
*Director of the United States Patent and Trademark Office*